US006677510B2

(12) United States Patent
Windham et al.

(10) Patent No.: US 6,677,510 B2
(45) Date of Patent: Jan. 13, 2004

(54) POWDERY MILDEW RESISTANT PLANTS

(75) Inventors: Mark T. Windham, Knoxville, TN (US); Robert N. Trigiano, Knoxville, TN (US); Willard T. Witte, Knoxville, TN (US)

(73) Assignee: University of Tennesse, Knoxville, TN (US)

( * ) Notice: Subject to any disclaimer, the term of this patent is extended or adjusted under 35 U.S.C. 154(b) by 0 days.

(21) Appl. No.: 09/878,693

(22) Filed: Jun. 11, 2001

(65) Prior Publication Data

US 2002/0035742 A1 Mar. 21, 2002

Related U.S. Application Data

(60) Provisional application No. 60/210,603, filed on Jun. 9, 2000.

(51) Int. Cl.[7] .......................... C12Q 1/68; C12P 19/34; C07H 21/04; A01H 5/00
(52) U.S. Cl. .......................... 800/323; 435/6; 435/91.2; 536/24.33
(58) Field of Search .................. 435/6, 91.2; 536/24.33

(56) References Cited

U.S. PATENT DOCUMENTS

| PP8,500 P | 12/1993 | Smith |
| PP10,166 P | 12/1997 | Nicholson |
| PP10,423 P | 6/1998 | Stanley |
| PP11,654 P | 11/2000 | Asako |

OTHER PUBLICATIONS

Trigiano et al., DNA amplification fingerprinting provides evidence that discula destructiva, the cause of dogwood anthracnose in North America, is an introduced pathogen, 1995, vol. 87(4), 490–500.*
Trigiano, R.N., et al., "Laboratory Exercises on DNA Amplification Fingerprinting for Evaluating the Molecular Diversity of Horticultural Species," HorTechnology, Jul.–Sep. 1998, pp. 413–423, vol. 8(3), U.S.
Caetano–Anolles, G., et al., "DNA amplification fingerprinting and marker screening for pseudo–testcress mapping of flowering dogwood (Cornus florida L.)", Euphytica, 1999, 106:209–222; Pub: Kluwer Academic Publishers, Netherlands.
Gary, L.B., "Appalachian Spring: New UT Cultivar is First to Resist Deadline Dogwood Disease," UT Ag. Magazine, Spring 1999, XP–002194700, Pub: Univ. of Tenn. Online.
Hagan, A.K., et al., "Susceptibility of Cultivars of Several Dogwood Taxa to Powdery Mildew and Spot Anthracnose", J. Environ. Hort., 1998, 16(3):147–151.
Hanson, S., "Dogwood: Current and Future Research", 2000, XP–002194703 [online].

Hollins, S.J., et al., "Breeding Disease Resistant Flowering Dogwood (Cornus florida)", SNA Reserach Conference, 1999, 44:359–361 [online].
Ragland, C., "Dogwood Tree", Dogwood, Microsoft® Encarta® Online Encyclopedia 2000, XP–002194704, Pub: Microsoft Corporation.
Trigiano, R.N., et al., "Teaching Methods: Laboratory Exercises on DNA Amplification Fingerprinting for Evaluating the Molecular Diversity of Horticultural Species," HorTechnology, 1998, 8(3):413–23, XP–001064538, Pub: Unknown.
Trigiano, R.N., et al., "Three New Cultivars of Flowering Dogwood Resistant to Powdery Mildew," Hort. Science, 2000, 35(3):490, #549, XP–001064539, Pub: Unknown.
Unknown, "Powdery Mildew of Flowering Dogwood", 2000, XP–002194701 [online], Pub: The University of Tennessee Dogwood Research Group.
Windham, M.T., et al., "Are 'Barton' and 'Cloud 9' the Same Cultivar of Cornus florida L. ?", J. Environ. Hort., 1998, 16(3):163–166, XP–001064563, Pub: unknown.
Windham, M.T., et al., "Development of Flowering Dogwood Cultivars Resistant to Powdery Mildew", Tenth Conference of Metropolitan Tree Improvement Alliance (Sep. – Oct. 1998), XP–002194702 [online].
Windham, M.T., et al., "Naturally Occurring Resistance to Powdery Mildew in Seedlings of Cornus florida", J. Environ. Hort., 1998, 16(3):173–175, XP–001064535, Pub: unknown.
Windham, M.T., et al., "New Dogwood Cultivars Resistant to Powdery Mildew", SNA Research Conference, 2000, 45:204–205, XP–002194698 [online].

* cited by examiner

Primary Examiner—Jeffrey Siew
Assistant Examiner—Joyce Tung
(74) Attorney, Agent, or Firm—Saliwanchik, Lloyd & Saliwanchik

(57) ABSTRACT

The subject invention provides plants with excellent resistance to powdery mildew. In a specific embodiment, the subject invention provides dogwood (Cornus florida) cultivars that are resistant to infestation with powdery mildew. Specifically exemplified herein are culitvars identified as 'Jean's Appalachian Snow', 'Kay's Appalachian Mist', and 'Karen's Appalachian Blush'. The present invention also provides materials and methods for identifying, characterizing, and/or producing powdery mildew resistant plants. In a specific embodiment, the subject invention provides polynucleotide sequences, and patterns of polynucleotide sequences, which are associated with resistance to powdery mildew. These polynucleotides are characteristic of the powdery mildew resistant plants as described herein. Such polynucleotides are particularly useful in identifying and characterizing plant having resistance to powdery mildew.

5 Claims, 3 Drawing Sheets

|  | AS | KAM | JAS | C9 | KAB | CP | SPR | CB |
|---|---|---|---|---|---|---|---|---|
| AS | 1.00 | | | | | | | |
| KAM | 0.80 | 1.00 | | | | | | |
| JAS | 0.76 | 0.76 | 1.00 | | | | | |
| C9 | 0.75 | 0.70 | 0.77 | 1.00 | | | | |
| KAB | 0.79 | 0.79 | 0.78 | 0.75 | 1.00 | | | |
| CP | 0.78 | 0.84 | 0.82 | 0.78 | 0.85 | 1.00 | | |
| SPR | 0.78 | 0.82 | 0.76 | 0.77 | 0.82 | 0.86 | 1.00 | |
| CB | 0.79 | 0.77 | 0.73 | 0.72 | 0.78 | 0.79 | 0.82 | 1.00 |

LEGEND: AS = 'Appalachian Spring', KAM = 'Kay's Appalachian Mist', JAS = 'Jean's Appalachian Snow', C9 = 'Cloud Nine', KAB = "Karen's Appalachian Blush', CP = 'Cherokee Princess', SPR = ' Springtime' and CB = 'Cherokee Brave'. All are white bract dogwoods except CB, which is red.

FIG. 1

POWDERY MILDEW RESISTANT PLANTS

CROSS-REFERENCE TO RELATED APPLICATION(S)

This application claims priority to U.S. Provisional Patent Application Ser. No. 60/210,603, filed Jun. 9, 2000, hereby incorporated by reference in its entirety.

BACKGROUND OF INVENTION

Powdery mildew is a common fungal disease of numerous ornamental plants (including dogwood, rose, phlox, and many bedding plants) that is commonly observed when atmospheric conditions provide warm days and cool nights. While powdery mildew does not always cause serious damage to an infected plant, it is capable of interfering with normal growth and reproduction. If the fungal infestation is severe enough, significant plant decline can be observed.

The powdery mildew fungus grows over the surface of tender leaf and stem tissues. The hyphae and conidia of the fungus cause the leaf to take on a white to gray appearance. Youngest leaves are typically infected first. Haustoria penetrate the leaf epidermal cells and act as anchors for the fungus. The haustoria also provide the fungus with water and nutrients taken from the plant. As a result of infection, the plant slowly declines. Dwarfing, distortion, chlorosis, premature senescence and browning of leaves, and blemished or aborted fruits and flowers are other manifestations of the fungal infestation. Infected plants will often produce new growth; infestation of this new growth with powdery mildew is governed by environmental conditions.

Chemical control is seldom recommended in the home landscape, however commercial operations depend upon chemical control in order to maintain salable plant materials. When chemical control is necessary, fungicides such as chlorothalonil (Daconil 2787), triadimefon (Fung-Away, Bayleton), propiconazole (Immunex), and triforine (Funginex, Triforine) are used. Fungicides protect healthy tissue from infection, however these same fungicides are incapable of curing infected tissue. Aside from the inability of the fungicides to kill powdery mildew, there are significant costs associated the use of fungicides in the control of this plant parasite. Typical fungicides used in the control of powdery mildew have costs in the hundreds of dollars per quart of fungicide. On a commercial scale, the nurseryman bears significant monetary costs to ensure that a salable material is maintained for consumption by the consumer.

Dogwoods have been particularly hard hit by powdery mildew. In Tennessee, a state that is known for its dogwoods, dogwoods are worth some $40 million to the state's economy each year. Dogwood anthracnose has wiped out dogwoods in Tennessee and all across the eastern United States. Unfortunately, publicity about dogwood problems have caused sales to plummet, even in areas of the country that have not been affected by dogwood anthracnose. The disease, which thrives in damp shady areas, has not only decimated dogwoods in some landscapes, it has also made a major dent in the nursery industry. The cost of producing dogwoods has gone up dramatically because of fungicide use. Producing dogwoods has become very expensive which, in the long run, means that the cost to consumers is increased.

In addition to being expensive, chemical control of powdery mildew is also undesirable from environmental and health perspectives. The active ingredients in many of the fungicides used in the control of this plant parasite are known carcinogens. Further, prolonged contact of these fungicides with the skin of the person applying the chemicals to the plant materials is known to be harmful. In some cases, allergic reactions are known to result. Many of these chemicals are also harmful to aquatic life and care must be exercised to prevent accidental contamination of soil and/or groundwater. Accordingly, it is of great interest to the industry to identify alternative means by which to confer resistance to infestation with powdery mildew.

BRIEF SUMMARY

The subject invention provides plants with excellent resistance to powdery mildew. In a specific embodiment, the subject invention provides dogwood (*Cornus florida*) cultivars that are resistant to infestation with powdery mildew. Specifically exemplified herein are cultivars identified as 'Jean's Appalachian Snow', 'Kay's Appalachian Mist', and 'Karen's Appalachian Blush'.

The present invention also provides materials and methods for identifying, characterizing, and/or producing powdery mildew resistant plants. In a specific embodiment, the subject invention provides polynucleotide sequences, and patterns of polynucleotide sequences, which are associated with resistance to powdery mildew. These polynucleotides are characteristic of the powdery mildew resistant plants as described herein. Such polynucleotides are particularly useful in identifying and characterizing plant having resistance to powdery mildew.

The polynucleotide sequences disclosed herein are useful in methods including, but not limited to, enhancing plant resistance to powdery mildew. The disclosed polynucleotide sequences are also useful in the identification of similar polynucleotide sequences in other varieties of powdery mildew resistant plants. The subject invention further pertains to the use of the disclosed polynucleotide sequences, or fragments thereof, in assays to characterize and/or identify genes associated with resistance to powdery mildew. Also contemplated according to the subject invention is the use of oligomers from these polynucleotide sequences in kits that can be used to identify genes that confer powdery mildew resistance.

Other aspects of the invention include use of polynucleotide sequences to produce purified polypeptides. Still further aspects of the invention use these purified polypeptides to produce antibodies or other molecules able to bind to the polypeptides. These antibodies or binding agents can then be used, for example, to analyze cells in order to localize the cellular distribution of polypeptides. The antibodies are also useful for the affinity purification of recombinantly produced polypeptides.

BRIEF DESCRIPTION OF DRAWINGS

FIG. 1. Similarity index between dogwood cultivars: AS='Appalachian Spring', KAM='Kay's Appalachian Mist', JAS='Jean's Appalachian Snow', C9='Cloud Nine', KAB='Karen's Appalachian Blush', CP='Cherokee Princess', SPR='Springtime' and CB='Cherokee Brave'. All are white bract dogwoods except CB, which is red.

DETAILED DESCRIPTION OF THE INVENTION

Figure 2:
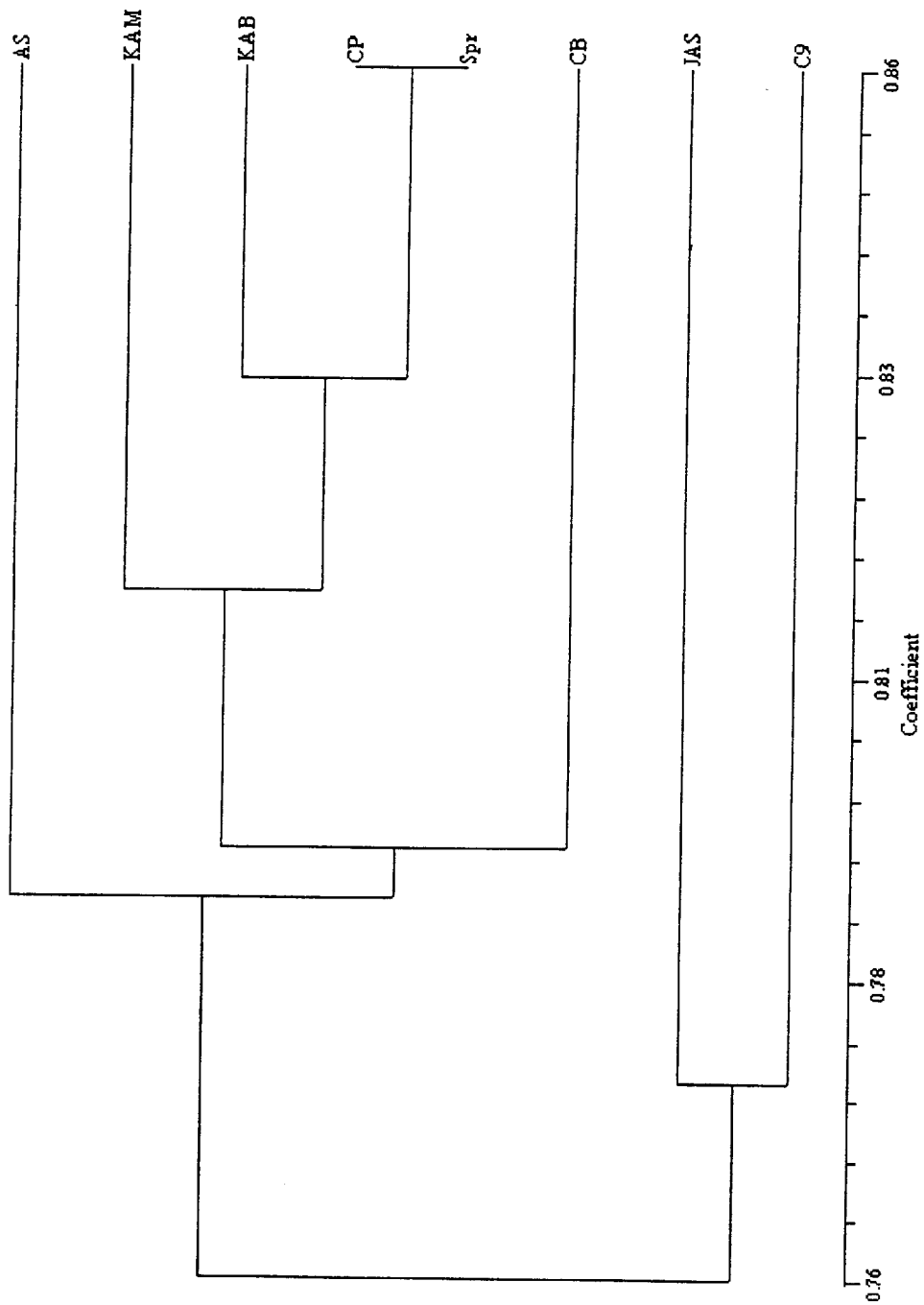
FIG. 2. Cluster analysis of dogwood cultivars: AS='Appalachian Spring', KAM='Kay's Appalachian Mist', JAS='Jean's Appalachian Snow', C9='Cloud Nine', KAB='Karen's Appalachian Blush', CP='Cherokee Princess', SPR='Springtime' and CB='Cherokee Brave'. All are white bract dogwoods except CB, which is red.

The present invention provides powdery mildew resistant plants. In a specific embodiment, the subject invention provides cultivars of flowering dogwood that are resistant to powdery mildew. The cultivars are derived from dogwoods botanically known as *Cornus florida*. Specifically exemplified herein are cultivars referred to by the names 'Jean's Appalachian Snow', 'Kay's Appalachian Mist', and 'Karen's Appalachian Blush'.

Powdery mildew (*Microsphaera pulchra*) of flowering dogwood (*Cornus florida* L.) has become a significant problem of trees in nursery production as well as in the landscape and forest of the eastern United States. The disease significantly reduces growth and berry production by older established trees and may contribute to the inability of younger trees (liners) in production to survive winter dormancy. Disease resistance in named cultivars is limited to partial resistance found in 'Cherokee Brave'—all other cultivars are extremely susceptible.

Until now the only disease control measure was to establish an expensive, labor-intensive, preventive fungicide program. We provide three dogwood cultivars that have been identified as extremely resistant to powdery mildew. 'Karen's Appalachian Blush' has long, non-overlapping, pink fringed bracts with a delicate appearance. 'Kay's Appalachian Mist' has creamy white, slightly overlapping bracts with deeply pigmented clefts. 'Jean's Appalachian Snow' has large, strongly overlapping bracts with non-pigmented clefts. The three powdery mildew resistant cultivars will be entered into an existing breeding program with 'Appalachian Spring', a cultivar released by the Tennessee Agriculture Experiment Station and resistant to dogwood anthracnose, in an attempt to produce trees that are resistant to both diseases.

'Jean's Appalachian Snow', 'Kay's Appalachian Mist', and 'Karen's Appalachian Blush' are white flowering dogwoods which have superior characteristics compared to other white flowering dogwoods with respect to powdery mildew resistance. Asexual reproduction of 'Jean's Appalachian Snow', 'Kay's Appalachian Mist', and 'Karen's Appalachian Blush' by terminal cuttings has shown that the unique and advantageous features of these new dogwood cultivars are stable and reproduced true to type in successive generations. Powdery mildew resistant plants according to the invention may be reproduced both asexually by cuttings and by seed.

A detailed description of the relevant features of each of the three cultivars specifically exemplified herein is as follows:

'Jean's Appalachian Snow' has white bracts that are overlapping. The bracts are similar in size to the bracts of the cultivar 'Cherokee Princess'. Upper pairs of bracts average about 15.8 cm long by about 11.2 cm wide in size (n=30). Clefts at the ends of the bracts are indented and have little pigmentation. Flower petals are yellow and flowers average 23 per inflorescence (n=15).

'Kay's Appalachian Mist' has creamy white bracts that slightly overlap. Average bract size is about 13.7 cm long by about 12.0 cm wide (n—14). Clefts at the ends of the bracts are flat and deeply pigmented. Flower petals are yellow and flowers average 22 per inflorescence (n=14).

'Karen's Appalachian Blush' has white bracts that pink along the edges. The bracts are long and floppy, do not overlap, and are delicate in appearance. Upper pairs of bracts average about 13.3 cm long by about 8.8 cm wide in size (n=30). Clefts at the ends of the bracts are pointed or flat and have little pigmentation. Flower petals are yellow and flowers average 20 per inflorescence (n=15).

In addition to providing specific dogwood cultivars, the present invention also provides materials and methods for identifying, characterizing and/or producing plants having resistance to powdery mildew. In a preferred embodiment, the powdery mildew resistant plants of the subject invention have particular nucleotide sequences and/or characteristic polynucleotide patterns.

The nucleotide sequences of the subject invention have numerous applications in techniques known to those skilled in the art of molecular biology having the benefit of the instant disclosure. These techniques include their use as hybridization probes, for chromosome and gene mapping, in PCR technologies, and in the production of sense or antisense nucleic acids. These examples are well known and are not intended to be limiting.

As a result of the degeneracy of the genetic code, a multitude of nucleotide sequences may be produced which are based upon particular peptide-, polypeptide-, or protein-encoding nucleotide sequences. Some of these will bear only minimal homology to the original sequence; however this invention specifically contemplates each and every possible variation of nucleotide sequence that could be made by selecting combinations based on possible codon choices. These combinations are made in accordance with the standard triplet genetic code and all such variations are to be considered as being specifically disclosed herein.

There are a variety of techniques, well known to those skilled in the art which can be used, in combination with the teachings provided herein to further identify, characterize and/or isolate polynucleotides (including RNA and DNA) associated with resistance to powdery mildew. For example, CLONTECH PCR-Select™ cDNA Subtraction (Clontech Laboratories, Inc., Palo Alto, Calif.) is one means by which differentially expressed genes may be isolated. The procedure allows for the isolation of transcripts present in one mRNA population that is absent, or found in reduced numbers, in a second population of mRNA. Rare transcripts may be enriched 1000-fold. This technique is useful for the isolation of those transcripts that are present in the mRNA population of powdery mildew resistant plants but absent in the mRNA populations of plants susceptible to powdery mildew infestation.

Other methods for the isolation of the genes that confer resistance to powdery mildew by comparison of DNA or RNA samples of resistant and non-resistant plants include those methods taught in U.S. Pat. No. 5,840,484; 5,882,874; 5,853,991; and 6,017,701. The teachings and citations of these patents are hereby incorporated by reference in their entireties.

The '484 patent teaches a method and system for quantifying the relative abundance of gene transcripts in a biological sample. The invention provides a method for comparing the gene transcript image analysis from two or more different biological samples in order to distinguish between the two samples and identify one or more genes that are differentially expressed between the two samples. One embodiment of the method generates high-throughput sequence-specific analysis of multiple RNAs or their corresponding cDNAs: gene transcript imaging analysis.

The '874 patent teaches a method for identifying differentially expressed nucleic acids between two samples, comprising: a) selecting a first and second nucleic acid sample; b) producing libraries for the first and second nucleic acid sample; c) performing reciprocal subtraction between the libraries to produce two subtracted libraries; d) amplifying the two subtracted libraries; and e) comparing the two amplified subtracted libraries to identify differentially expressed nucleic acids. This patent also teaches means for the isolation of nucleic acids identified by the above-described methods, wherein the nucleic was not previously known to be differentially expressed between the two samples.

The '991 patent teaches anchored PCR-based cDNA subtractive (PCSUB) libraries. These libraries are made by generating two cDNA libraries with anchored ends, one of tester DNA and one of driver DNA. The two libraries would undergo subtractive hybridization and amplification. In addition to using dephoshorylated adaptors that prevents amplification of driver DNA, a biotin-tagged driver library, using for example biotin labeled dCTP during PCR, allows for a physical separation (using streptavidin-coated beads) of driver and of driver/tester hybrid cDNA from the desired and amplified target cDNA. This enhances the relative amplification of target cDNA. The removal of the driver cDNA also allows for a higher ratio of driver/tester cDNA, and therefore more stringent subtraction of cDNA sequences which are not unique to the target cDNA. More importantly, the PCSUB method results in a library representing differentially expressed mRNAs.

The '701 patent provides simplified methods to create normalized and subtractive nucleic acid populations. This patent provides methods to generate powerful new libraries that also facilitate the discovery of new genes. These libraries may be used directly or in subtractive protocols to produce other nucleic acid libraries.

The polynucleotide sequences thus identified are useful in a variety of protocols which include the recombinant production of polypeptides encoded by the polynucleotide sequences, transfection of cells, preferably plant cells, whereby resistance to powdery mildew infestation is conferred, and screening assays of other nucleic acid samples for analogs of those nucleic acids which confer resistance to powdery mildew. Recombinant nucleotide variants are specifically contemplated in this aspect of the invention.

Polynucleotide sequences associated with powdery mildew resistance as described herein can be used as probes in assays and in procedures to identify, characterize and isolate related genes. As used herein, "Probes" refer to nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and designed to have specificity in PCR, hybridization membrane-based, or ELISA-like technologies. The probes of this invention allow for the identification and isolation of other genes that provide resistance to powdery mildew.

A "portion" or "fragment" of a polynucleotide or nucleic acid comprises all or any part of the nucleotide sequence having fewer nucleotides than about 6 kb, preferably fewer than about 1 kb which can be used as a probe. Such probes may be labeled with reporter molecules using nick translation, Klenow fill-in reaction, PCR or other methods well known in the art. After pretesting to optimize reaction conditions and to eliminate false positives, nucleic acid probes may be used in Southern, northern or in situ hybridizations to determine whether target DNA or RNA is present in a biological sample, cell type, tissue, organ or organism.

An "oligopeptide" is a short stretch of amino acid residues and may be expressed from an oligonucleotide. It may be functionally equivalent to and either the same length as or considerably shorter than a "fragment," "portion," or "segment" of a polypeptide. Such sequences comprise a stretch of amino acid residues of at least about 5 amino acids and often about 17 or more amino acids, typically at least about 9 to 13 amino acids, and of sufficient length to display biologic and/or immunogenic activity.

"Recombinant polypeptide variant" refers to any polypeptide that differs from naturally occurring peptide, polypeptide, or protein by amino acid insertions, deletions and/or substitutions. Guidance in determining which amino acid residues may be replaced, added or deleted without abolishing characteristics of interest may be found by comparing the sequence of the peptide, polypeptide, or protein with that of related polypeptides and minimizing the number of amino acid sequence changes made in highly conserved regions.

Amino acid "substitutions" are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid "insertions" or "deletions" are changes to or within an amino acid sequence. They typically fall in the range of about 1 to 5 amino acids. The variation allowed in a particular amino acid sequence may be experimentally determined by producing the peptide synthetically or by systematically making insertions, deletions, or substitutions of nucleotides in the sequence using recombinant DNA techniques.

Polynucleotide sequences useful according to the subject invention can be obtained in a variety of ways. For example, the sequences may be isolated from their natural sources as described herein. It is also possible to produce these sequences, or portions thereof, entirely by synthetic chemistry. After synthesis, the nucleic acid sequence can be used alone or joined with a preexisting sequence and inserted into one of the many available DNA vectors and their respective host cells using techniques well known in the art. Moreover, synthetic chemistry may be used to introduce specific mutations into the nucleotide sequence. Alternatively, a portion of sequence in which a mutation is desired can be synthesized and recombined with a portion of an existing genomic or recombinant sequence.

Nucleic acids which confer resistance to powdery mildew may be introduced into target plant cells according to the subject invention by any of the well known DNA delivery methods, such as electroporation, electrophoresis, microinjection, micro-projectile bombardment, micro-LASER beam-induced perforation of cell wall, or simply by incubation. Introduction of these nucleic acids into the genome of the plant cells, along with any other desired nucleic acids such as promoters and/or enhancers of gene expression, will provide the targeted plant cell with resistance to powdery mildew. Accordingly, the subject invention also provides for methods of producing powdery mildew resistant plants, particularly woody ornamentals, comprising the introduction of nucleic acid sequences, which confer resistance to this pathogen, via the aforementioned methods of introducing nucleic acids into target plant cells. Plants to which these methods are applicable include, and are not limited to dogwood, rose, phlox, and many bedding plants. In a preferred embodiment, the plants to which this methodology is applicable are woody ornamentals.

The nucleotide sequences of the subject invention can be used individually, or in panels, in a test or assay to detect levels of peptide, polypeptide, or protein expression. The form of such qualitative or quantitative methods may include northern analysis, dot blot or other membrane based technologies, dip stick, pin or chip technologies, PCR, ELISAs or other multiple sample format technologies.

The instant invention also contemplates methods for recombinantly producing peptides, polypeptides, or proteins encoded by the nucleic acids that confer resistance to powdery mildew. An entire or partial nucleotide sequence encoding a peptide, polypeptide, or protein as disclosed herein may be used to produce an amino acid sequence using well known methods of recombinant DNA technology. In this embodiment of the invention, the nucleic acids are inserted into vectors that provide for expression in a desired host cell expression system. Vectors and host cell expression systems and methods of culturing said host cells are well known to those skilled in the art. It may be advantageous to produce peptide, polypeptide, or protein-encoding nucleotide sequences possessing a substantially different codon usage. Codons can be selected to increase the rate at which expression of the peptide occurs in a particular prokaryotic or eukaryotic expression host in accordance with the frequency with which particular codons are utilized by the host. The host cells may be used to produce chimeric polypeptides, recombinant polypeptide variants, oligopeptides, and peptides, polypeptides, or proteins that contain amino acid substitutions, additions, and/or deletions.

The present invention also contemplates antibodies that specifically bind to the peptides, polypeptides, and/or proteins of the subject invention. The term "antibody" encompasses polyclonal and monoclonal antibody preparations, as well as preparations including hybrid antibodies, genetically altered antibodies (including antibodies fused to toxins, antibodies modified to alter their physiochemical characteristics, and antibodies subjected to affinity mutagenesis), F(ab')$_2$ fragments, F(ab) fragments, F$_v$, fragments, single domain antibodies, chimeric antibodies, diabodies, multispecific antibodies, humanized antibodies, and functional fragments thereof which exhibit immunological binding properties of the parent antibody molecule. Methods of making polyclonal and monoclonal antibodies are known in the art.

Antibodies produced according to the invention are useful in affinity purification of recombinantly produced peptides or in immunoassays identifying the presence of the recombinantly produced peptides in transformed cells or culture supernates. The antibodies may also be used to isolate naturally occurring peptides, polypeptides, and proteins from plant tissue by affinity chromatography, antibody mediated precipitation, or other methods known to the routineer.

Since the list of technical and scientific terms cannot be all encompassing, any undefined terms shall be construed to have the same meaning as is commonly understood by one of skill in the art to which this invention belongs. Furthermore, the singular forms "a", "an" and "the" include plural referents unless the context clearly dictates otherwise.

Following are examples that illustrate procedures for practicing the invention. These examples should not be construed as limiting. All percentages are by weight and all solvent mixture proportions are by volume unless otherwise noted.

EXAMPLE 1

'Jean's Appalachian Snow', 'Kay's Appalachian Mist', and 'Karen's Appalachian Blush' are superior in resistance to powdery mildew to other white flowering dogwood cultivars. These cultivars have been tested for resistance to powdery mildew for four (4), three (3), and three (3) years, respectively. Test plants were exposed to powdery mildew and assessed for resistance to powdery mildew. Mildew scores for 'Jean's Appalachian Snow', 'Kay's Appalachian Mist', 'Karen's Appalachian Blush', control plants, and 'Cherokee Brave' were obtained using the following scale: 0=healthy; 1=≦2% of foliage with signs or symptoms of powdery mildew; 2=≦10% of foliage with signs or symptoms of powdery mildew; 3=≦25% of foliage with signs or symptoms of powdery mildew; 4=≦50% of foliage with signs or symptoms of powdery mildew; 5=≦75% of foliage with signs or symptoms of powdery mildew; 6=≦100% of foliage with signs or symptoms of powdery mildew. Tables 1–3 present the data obtained over the test period.

TABLE 1

Resistance to Powdery Mildew: 'Jean's Appalachian Snow'

| Year | 'Jean's Appalachian Snow' | Control Score[1] | 'Cherokee Brave'[2] |
|---|---|---|---|
| 1995 | 0.0 | 5.0(a) | — |
| 1996 | 0.0 | 5.0(b) | 1.2 |
| 1997 | 0.0 | 4.6(b) | 2.3 |
| 1998 | 0.0 | 4.8(c) | 2.1 |

[1]Control plants were (a) *Cornus florida* seedlings, (b) 'Cherokee Sunset', or (c) 'Cherokee Daybreak' that were or similar age and size.
[2]'Cherokee Brave' is a pink flowering dogwood cultivar which is the only cultivar known to the inventors to possess resistance to powdery mildew.

TABLE 2

Resistance to Powdery Mildew: 'Kay's Appalachian Mist'

| Year | 'Kay's Appalachian Mist' | Control Score[1] | 'Cherokee Brave'[2] |
|---|---|---|---|
| 1996 | 0.0 | 5.0(a) | — |
| 1997 | 0.0 | 4.6(b) | 2.3 |
| 1998 | 0.0 | 4.8(b) | 2.1 |

[1]Control plants were (a) *Cornus florida* seedlings or (b) 'Cherokee Sunset' that were of similar age and size.
[2]'Cherokee Brave' is a pink flowering dogwood cultivar which is the only cultivar known to the inventors to possess resistance to powdery mildew.

TABLE 3

Resistance to Powdery Mildew: 'Karen's Appalachian Blush'

| Year | 'Karen's Appalachian Snow' | Control Score[1] | 'Cherokee Brave'[2] |
|---|---|---|---|
| 1996 | 0.0 | 5.8(a) | — |
| 1997 | 0.0 | 6.0(b) | 2.3 |
| 1998 | 1.0 | 4.8(c) | 2.1 |

[1]Control plants were (a) *Cornus florida* seedlings, (b) 'Cherokee Sunset', or (c) 'Cherokee Daybreak' that were of similar age and size.
[2]'Cherokee Brave is a pink flowering dogwood cultivar which is the only cultivar known to the inventors to possess resistance to powdery mildew.

EXAMPLE 2

Figure 3:
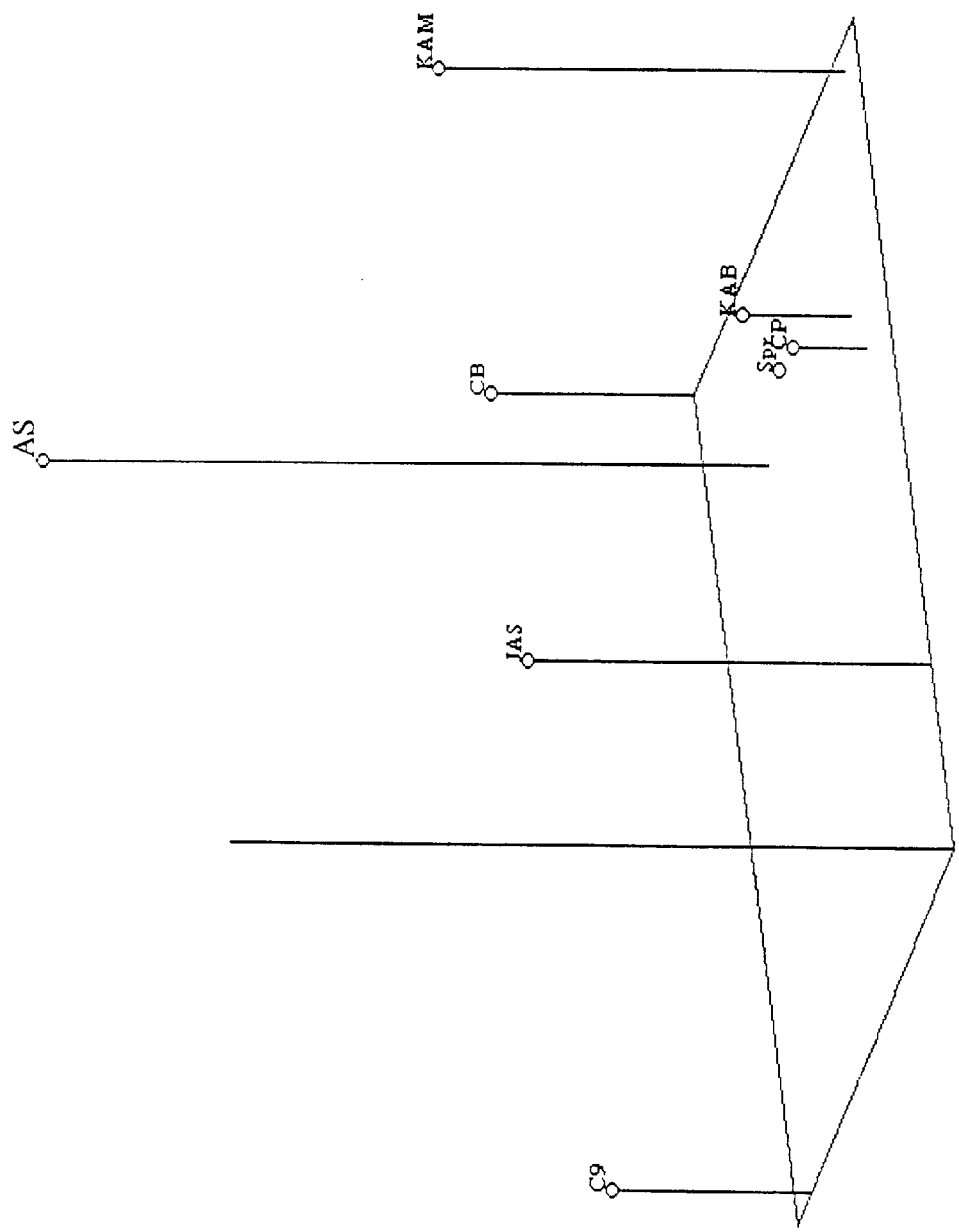
FIG. 3. Principal coordinate analysis of dogwood cultivars: AS='Appalachian Spring', KAM='Kay's Appalachian Mist', JAS='Jean's Appalachian Snow', C9='Cloud Nine', KAB='Karen's Appalachian Blush', CP='Cherokee Princess', SPR='Springtime' and CB='Cherokee Brave'. All are white bract dogwoods except CB, which is red.

DNA amplification fingerprinting was used to type 'Jean's Appalachian Snow', 'Kay's Appalachian Mist', and 'Karen's Appalachian Blush'. The methodology followed that of Trigiano and Caetano-Anollés (HortTechnology, 8:413–423 [1998]). Data, obtained from 235 loci generated from genomic DNA using seven (7) arbitrary octomeric primers, was used to compare the powdery mildew resistant dogwoods of the subject application to other dogwoods (including powdery mildew resistant lines and cultivars commonly found in nurseries). The sequences of the primers were as follows: 1) GAGCCTGT, 2) GTTACGCC, 3) CCTGTGAG, 4) GTAACGCC, 5) GACGTAGG, 6) GATCGCAG, AND 7) GTATCGCC. DNA amplification fingerprinting analysis as well as the cluster and principal coordinate analysis were completed using the NTSYS PROGRAM, pc version 2.2 (Exeter Software, 100 N. Country Road, Sedtauket, N.Y. 11733). A similarity index is provided in FIG. 1. FIG. 2 depicts the resulting cluster analysis. FIG. 3 depicts the principal coordinate analysis of the relationships between the dogwoods.

The abbreviations found in the Figures are as follows: AS='Appalachian Spring', KAM='Kay's Appalachian Mist', JAS='Jean's Appalachian Snow', C9='Cloud Nine', KAB='Karen's Appalachian Blush', CP='Cherokee Princess', SPR='Springtime' and CB='Cherokee Brave'. All are white bract dogwoods except CB, which is red.

EXAMPLE 3

Polynucleotide sequences encoding proteins can be isolated by PCR-Select™ cDNA Subtraction (Clontech Laboratories, Inc., Palo Alto, Calif.). First, mRNA populations can be isolated from powdery mildew resistant dogwood cultivars and dogwood cultivars susceptible to infestation by powdery mildew. These mRNA populations can then be converted into cDNA. cDNA prepared from powdery mildew resistant dogwoods were designated "tester" transcripts and the reference cDNA as "driver" (cDNA prepared from powdery mildew susceptible dogwoods). Tester and driver cDNA are hybridized, and the hybridized sequences are then removed. Consequently, the remaining unhybridized cDNAs represent genes that are expressed in the tester, but are absent from the driver mRNA. After the subtracted cDNA is obtained, sequencing can be performed and analyzed by sequence similarity searches in various databases. Function can also be determined by analysis of the expression of these genes under normal growth and development conditions and for the ability of the isolated genes to protect against powdery mildew infestation.

EXAMPLE 4

Insertion of Genes into Plants

One aspect of the subject invention is the transformation of plants with the subject polynucleotide sequences.

Obviously, a promoter region capable of expressing the gene in a plant is needed. Thus, for in planta expression, the DNA of the subject invention is under the control of an appropriate promoter region. Techniques for obtaining in planta expression by using such constructs is known in the art.

Genes can be inserted into plant cells using a variety of techniques that are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the polynucleotide sequence can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids.

Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker that are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

It should be understood that the examples and embodiments described herein are for illustrative purposes only and that various modifications or changes in light thereof will be suggested to persons skilled in the art and are to be included within the spirit and purview of this application and the scope of the appended claims. All patents, patent applications, provisional applications, and publications referred to or cited herein are incorporated by reference in their entirety to the extent they are not inconsistent with the explicit teachings of this specification.

What is claimed is:

1. A method of identifying powdery mildew resistant dogwood plants comprising:
   a. conducting DNA amplification fingerprinting (DAF) of genetic material obtained from a dogwood plant; and
   b. comparing the DNA fingerprint of said plant with the DNA fingerprint of a powdery mildew resistant dogwood, selected from the group consisting of 'Jean's Appalachian Snow', 'Kay's Appalachian Mist', and 'Karen's Appalachian Blush' to identify said powdery mildew resistant dogwood.

2. The method according to claim 1, wherein said fingerprinting is performed using arbitrary primers.

3. The method according to claim 2, wherein said primers are octomeric.

4. The method according to claim 3, wherein said DAF is performed using the following combination of primers: 1) GAGCCTGT, 2) GTTACGCC, 3) CCTGTGAG, 4) GTAACGCC, 5) (GACGTAGG, 6) GATCGCAG, and 7) GTATCGCC.

5. A method of identifying powdery mildew resistant dogwood plants comprising:
   a. conducting DNA amplification fingerprinting (DAF) of genetic material obtained from a dogwood plant; and
   b. comparing the DNA fingerprint of said plant with the DNA fingerprint of a powdery mildew resistant dogwood to identify said powdery mildew resistant dogwood;
   wherein said DAF is performed using the following combination of arbitrary octomeric primers: 1) GAGCCTGT, 2) GTTACGCC, 3) CCTGTGAG, 4) GTAACGCC, 5) GACGTAGG, 6) GATCGCAG, and 7) GTATCGCC.

* * * * *

UNITED STATES PATENT AND TRADEMARK OFFICE
CERTIFICATE OF CORRECTION

PATENT NO. : 6,677,510 B2
DATED : January 13, 2004
INVENTOR(S) : Mark T. Windham, Robert N. Trigiano and Willard T. Witte It is certified that error appears in the above-identified patent and that said Letters Patent is hereby corrected as shown below:

<u>Column 3,</u>
Line 65, "(-14)" should read -- (=14) --.

<u>Column 4,</u>
Line 54, "U.S. Pat. No. 5,840,484" should read -- U.S. Pat. Nos. 5,840,484; 5,882,874; 5,853,991; and 6,017,701 --.

<u>Column 8,</u>
Lines 17, 18, 19, 20, 21 and 22, "$\leqq$" should read -- $\leq$ --.
Line 52, Table 3, column 2 heading, "'Karen's Appalachian Snow'" should read -- 'Karen's Appalachian Blush' --.

Signed and Sealed this

Eighteenth Day of May, 2004

JON W. DUDAS
*Acting Director of the United States Patent and Trademark Office*

```
                           SEQUENCE LISTING

<160> NUMBER OF SEQ ID NOS: 7

<210> SEQ ID NO 1
<211> LENGTH: 8
<212> TYPE: DNA
<213> ORGANISM: Random Primer

<400> SEQUENCE: 1 gagcctgt                                                                  8

<210> SEQ ID NO 2
<211> LENGTH: 8
<212> TYPE: DNA
<213> ORGANISM: Random Primer

<400> SEQUENCE: 2 gttacgcc                                                                  8

<210> SEQ ID NO 3
<211> LENGTH: 8
<212> TYPE: DNA
<213> ORGANISM: Random Primer

<400> SEQUENCE: 3 cctgtgag                                                                  8

<210> SEQ ID NO 4
<211> LENGTH: 8
<212> TYPE: DNA
<213> ORGANISM: Random Primer

<400> SEQUENCE: 4 gtaacgcc                                                                  8

<210> SEQ ID NO 5
<211> LENGTH: 8
<212> TYPE: DNA
<213> ORGANISM: Random Primer

<400> SEQUENCE: 5 gacgtagg                                                                  8

<210> SEQ ID NO 6
<211> LENGTH: 8
<212> TYPE: DNA
<213> ORGANISM: Random Primer

<400> SEQUENCE: 6 gatcgcag                                                                  8

<210> SEQ ID NO 7
<211> LENGTH: 8
```

```
<212> TYPE: DNA
<213> ORGANISM: Random Primer

<400> SEQUENCE: 7 gtatcgcc                                                                  8
```